United States Patent [19]
Bernards et al.

[11] Patent Number: 6,033,843
[45] Date of Patent: Mar. 7, 2000

[54] INTERACTION OF CYCLIN D1 AND ESTROGEN RECEPTOR AND ITS USE IN ASSAYS

[75] Inventors: René Bernards, Alconde; Rob J. A. M. Michalides, Purmerend; Renate M. L. Zwijsen, Utrecht, all of Netherlands

[73] Assignee: Prolifix, Limited, United Kingdom

[21] Appl. No.: 09/171,151

[22] PCT Filed: Apr. 16, 1997

[86] PCT No.: PCT/EP97/01888

§ 371 Date: Apr. 6, 1999

§ 102(e) Date: Apr. 6, 1999

[87] PCT Pub. No.: WO97/40378

PCT Pub. Date: Oct. 30, 1997

[30] Foreign Application Priority Data

Apr. 19, 1996 [GB] United Kingdom .................. 9608143

[51] Int. Cl.[7] .......................... C12N 15/09; C12N 15/16; C12Q 1/00; C12Q 1/02
[52] U.S. Cl. ................. 435/4; 435/7.1; 435/7.2; 435/7.21; 435/7.23; 435/7.8; 435/41; 435/69.1; 435/69.4; 435/69.7; 435/70.1; 435/70.3
[58] Field of Search .................. 435/4, 7.1, 7.2, 435/7.23, 7.8, 41, 69.1, 69.4, 69.7, 70.1, 70.3

[56] References Cited

FOREIGN PATENT DOCUMENTS

WO 94/10307   5/1994   WIPO.

OTHER PUBLICATIONS

Zwijsen et al., *Cell*, 88(3):405–415 (1997).
Van Diest et al., *Am. J. Pathol.*, 150(2):705–711 (1997).
Wilcken et al., *Clin. Cancer Res.*, 3(6):849–854 (1997).
International Search Report.

*Primary Examiner*—Nancy A. Johnson
*Assistant Examiner*—Alana M. Harris
*Attorney, Agent, or Firm*—Banner & Witcoff, Ltd.; Kathleen M. Williams

[57] ABSTRACT

The present invention relates to the finding that cyclin D1 interacts with estrogen receptor to provide activation of estrogen responsive genes. The present invention provides in vitro and in vivo assays to measure the interaction. The in vivo assays may be conducted in cells which grow in response to estrogen, particularly breast tumour cells.

9 Claims, 6 Drawing Sheets

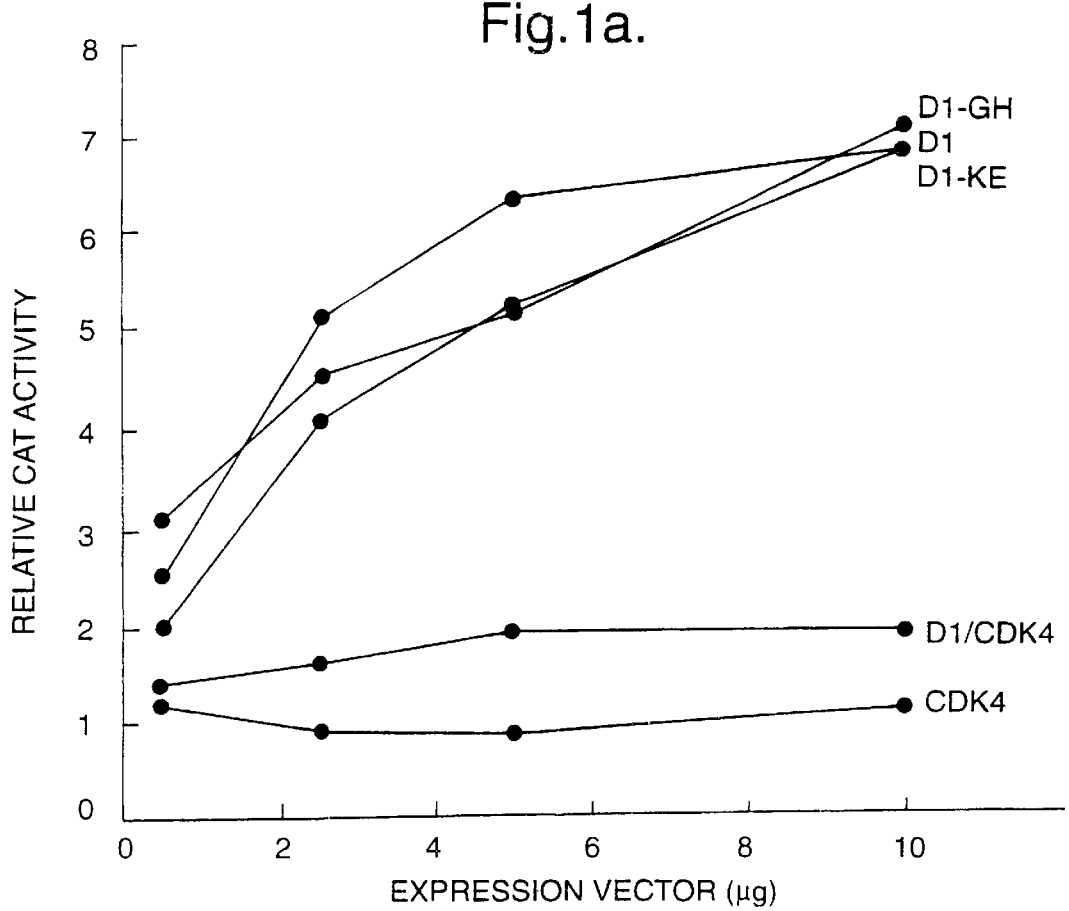

INTERACTION OF CYCLIN D1 AND ESTROGEN RECEPTOR AND ITS USE IN ASSAYS

The present invention relates to methods for preventing the growth of tumours, and for assays for compounds useful in the prevention of tumours.

BACKGROUND OF THE INVENTION

The cyclins are a class of polypeptides which are involved in the control of the cell cycle. Three closely related human D-type cyclins have been identified, all of which interact with and activate cyclin dependent kinases (CDK) 4 and 6, although they have specialized function in distinct cell types. The cyclin D1 gene has been found to be overexpressed and/or deregulated by clonal chromosome rearrangements or by amplification in B cell lymphoma, in parathyroid adenoma, and in breast and squamous cell cancer. It has also recently been shown that cyclin D1 deficient mice have a defect in estrogen-mediated proliferation of breast epithelium during pregnancy (Sicinski et al, 1995, Cell 82; 621–630; Fantl et al, 1995, Genes & Development 9; 2364–2372).

DISCLOSURE OF THE INVENTION

We have investigated the mechanisms of cyclin D1 regulation of cell growth and found that this protein interacts directly with the estrogen receptor (ER) and potentiates the transcription of estrogen receptor-regulated genes. Transcription is increased by formation of cyclin D1-ER complex which binds to the estrogen response element (ERE) found upstream of estrogen responsive genes. This finding provides a target for the control of cell proliferation, particularly in those cells which grow in response to stimulation by estrogen, e.g. breast tumour cells. Thus the present invention is useful for assaying for potential inhibitors of the growth of estrogen responsive tumour cells, particularly those in which cyclin D1 is found at elevated levels. Elevated levels of cyclin D1 may occur for a variety of reasons, e.g. over expression of a single cyclin D1 gene or by gene amplification. Thus in a first aspect the present invention provides an assay for inhibitors of estrogen responsive tumour cells which comprises:

a) bringing into contact a cyclin D1, an estrogen receptor and a putative inhibitor compound under conditions where the cyclin D1 and the estrogen receptor, in the absence of inhibitor, are capable of forming a complex which is capable of binding to an estrogen response element;

b) providing an estrogen response element to which the complex is capable of binding and transcriptionally activating; and c) measuring the degree of inhibition of binding or transcriptional activation caused by said inhibitor compound.

The present invention further provides an assay for an inhibitor of estrogen responsive tumour cells which comprises:

a) bringing into contact a cyclin D1, an estrogen receptor and a putative inhibitor compound under conditions where the cyclin and the estrogen receptor, in the absence of inhibitor, are capable of forming a complex; and b) measuring the degree of inhibition of complex formation caused by said inhibitor compound.

In a further aspect, the invention provides compounds obtainable by such an assay, for example peptide compounds based on the portions of cyclin D1 or the estrogen receptor which interact with each other.

The assay of the invention is optionally performed in the presence of an estrogen which is capable of binding to the estrogen receptor.

BRIEF DESCRIPTION OF THE DRAWINGS

FIGS. 1A–1E shows that cyclin D1 potentiates ERE responsive gene transcription in the presence of 17β-estradiol.

DETAILED DESCRIPTION OF THE INVENTION

Figure 1C:
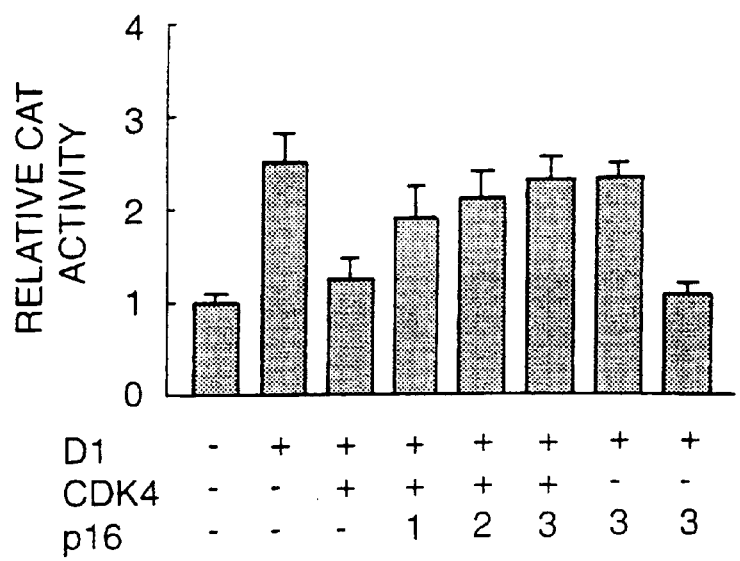

The cyclin D1 may be any suitable mammalian cyclin D1, particularly human cyclin D1. Human D1 cyclin has been cloned and sources of the gene can be readily identified by those of skill in the art. See for example, Xiong et al, 1991, Cell 65; 691–699 and Xiong et al, 1992, Genomics 13; 575–84. Murine D1 cyclin has also been cloned. Other mammalian cyclins can be obtained using routine cloning methods analogous to those described in the aforementioned references.

Although wild-type cyclin D1 is preferred mutants of D1 which still retain the ability to interact directly with the estrogen receptor may also be used. Examples of cyclin D1 mutants are well known in the art and two particular mutants are illustrated in the accompanying Examples. A particularly preferred mutant is a mutant which carries a mutation in the cyclin box, such as the cyclin D1-KE mutant. This mutation renders the D1 unable to bind CDKs.

It is not necessary to use the entire cyclin D1 proteins for assays of the invention. Fragments of the cyclin may be used provided such fragments retain the ability to interact with the target domain of the estrogen receptor responsible for the cyclin interaction. Fragments of cyclin D1 may be generated in any suitable way known to those of skill in the art. Suitable ways include, but are not limited to, recombinant expression of a fragment of the DNA encoding the cyclin. Such fragments may be generated by taking DNA encoding the cyclin, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Small fragments of the cyclin (up to about 20 or 30 amino acids) may also be generated using peptide synthesis methods which are well known in the art.

The ability of suitable fragments to bind to the estrogen receptor (or fragment thereof) may be tested using routine procedures such as those described in the accompanying examples relating to intact cyclin D1. Reference herein to cyclin D1 includes the above mentioned mutants and fragments which are functionally able to bind the estrogen receptor unless the context is explicitly to the contrary.

The estrogen receptor used in the assay obtained from the same mammalian source as the cyclin D1. The human estrogen receptor is preferred. This is a 66 kd protein which functions as hormone-activated transcription factor. Receptor activation is thought to be a consequence of ligand-induced conformational changes in the structure of the receptor. The complex of estrogen with its receptor binds with a high affinity to a well-defined 13-bp palindromic sequence, the estrogen response element (ERE). The ERE is usually located upstream of an estrogen-responsive gene. Estrogen responsive genes include progesterone receptor and PS-2. Transcriptional activation of these genes is involved in estrogen-responsive tumour growth.

Although the estrogen receptor may be provided in free from it may also be used in the form of a fusion protein linked to marker or reporter proteins. For example, in a preferred embodiment of the invention the estrogen receptor may be fused to a heterologous DNA binding domain such as that of the yeast transcription factor GAL 4. The GAL 4 transcription factor comprises two functional domains. These domains are the DNA binding domain (DBD) and the transcriptional activation domain (TAD). By fusing the estrogen receptor to one of those domains and the cyclin D1 to the other domain, a functional GAL 4 transcription factor is restored only when two proteins of interest interact. Thus, interaction of the proteins may be measured by the use of a reporter gene probably linked to a GAL 4 DNA binding site which is capable of activating transcription of said reporter gene. This assay format is described by Fields and Song, 1989, Nature 340; 245–246. This type of assay format can be used in both mammalian cells and in yeast and is described in further detail in the Examples which follow.

Fragments and mutants of the estrogen receptor which retain the ability to interact with the cyclin D1 may also be used, and such fragments and mutants may be obtained by methods analogous to those described above in relation to cyclin fragments. Particularly preferred fragments include those which retain the E/F regions comprising amino acids 292–595 or a portion thereof such as 340–595 of the ER. Smaller fragments may also be used, e.g. those starting at around 292, 300, 340, 360 or 380 and ending at the C-terminus (595) or a truncation thereof, e.g. 590, 580, 550 or 500. Suitable fragments may be determined by routine experimentation. Reference herein to the estrogen receptor includes fragments and mutants which retain the ability to interact with cyclin D1 unless the context is explicitly to the contrary. In this context, "interact" includes binding to ER, the minimum requirement for an in vitro assay. For in vitro or in vivo assays which rely on the D1-ER dimer binding to an ERE and activating transcription, the necessary interaction must provide this.

Although our studies have found that the estrogen receptor is activated by cyclin D1 alone to provide ERE-responsive gene transcription we have found that transcription is enhanced synergistically in the presence of an estrogen. It is thus a preferred aspect of the assay that estrogen is also brought into contact with the cyclin D1, estrogen receptor and putative inhibitor compound. The estrogen may be any natural or synthetic estrogen capable of binding to and activating the estrogen receptor. Examples of estrogens include 17β-estradiol.

The interaction between cyclin D1 and the estrogen receptor may be studied in vitro by labelling one of these proteins with a detectable label and bringing it into contact with the other protein which has been optionally immobilised on a solid support, either prior to or after the proteins have been brought into contact with each other. Suitable detectable labels include $^{35}$S-methionine which may be incorporated into recombinantly produced proteins, and tags such as an HA tag, GST or histidine. The recombinantly produced protein may also be expressed as a fusion protein containing an epitope which can be labelled with an antibody. Alternatively, an antibody against the cyclin and/or ER can be obtained using conventional methodology.

Figure 4A:
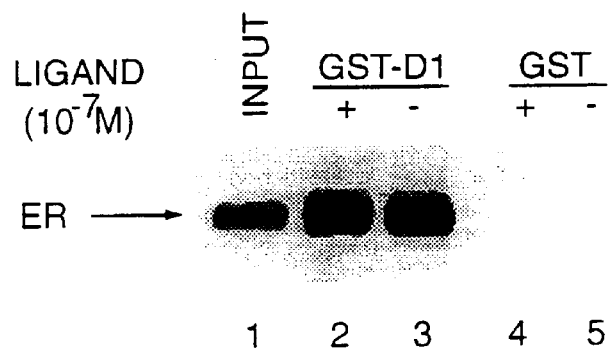
FIGS. 4A–4C show cyclin D1 interacts with (un)liganded ER.

The protein which is optionally immobilized on a solid support may be immobilized using an antibody against that protein bound to a solid support or via other technologies which are known per se. In the Examples which follow a preferred in vitro interaction is illustrated which utilises a fusion protein of cyclin D1 fused to glutathione-S-transferase (GST) This may be immobilized on glutathione agarose beads. In an in vitro assay format of the type described above the putative inhibitor compound can be assayed by determining its ability to diminish the amount of labelled ER which binds to the immobilized GST-cyclin D1. This may be determined by fractionating the glutathione-agarose beads by SDS-polyacrylamide gel electrophoresis. Alternatively, the beads may be rinsed to remove unbound protein and the amount of protein which has bound can be determined by counting the amount of label present in, for example, a suitable scintillation counter. It can be seen that in this alternative in vitro format it is not necessary to provide an ERE in order to measure the binding between the cyclin D1 and the ER; such binding may be measured directly. An example of this is indicated in FIG. 4a.

In an alternative mode, the one of the cyclin D1 and the ER may be labelled with a fluorescent donor moiety and the other labelled with an acceptor which is capable of reducing the emission from the donor. This allows an assay according to the invention to be conducted by fluorescence resonance energy transfer (FRET). In this mode, the fluorescence signal of the donor will be altered when the cyclin D1 and ER interact. The presence of a candidate inhibitor compound which disrupts the interaction will increase the amount of unaltered fluorescence signal of the donor.

FRET is a technique known per se in the art and thus the precise donor and acceptor molecules and the means by which they are linked to the cyclin D1 and ER may be accomplished by reference to the literature.

Suitable fluorescent donor moieties are those capable of transferring fluorogenic energy to another fluorogenic molecule or part of a compound and include, but are not limited to, coumarins and related dyes such as fluoresceins, rhodols and rhodamines, resorufins, cyanine dyes, bimanes, acridines, isoindoles, dansyl dyes, aminophthalic hydrazines such as luminol and isoluminol derivatives, aminophthalimides, aminonaphthalimides, aminobenzofurans, aminoquinolines, dicyanohydroquinones, and europium and terbium complexes and related compounds.

Suitable acceptors include, but are not limited to, coumarins and related fluorophores, xanthenes such as fluoresceins, rhodols and rhodamines, resorufins, cyanines, difluoroboradiazaindacenes, and phthalocyanines.

A preferred donor is fluorescein and preferred acceptors include rhodamine and carbocyanine. The isothiocyanate derivatives of these fluorescein and rhodamine, available from Aldrich Chemical Company Ltd, Gillingham, Dorset, UK, may be used to label the cyclin D1 and ER. For attachment of carbocyanine, see for example Guo et al, J. Biol. Chem., 270; 27562–8, 1995.

The assay of the invention may also take the form of an in vivo assay. The in vivo assay may be performed in an estrogen responsive cell line which expressing the estrogen receptor or in ER-negative cell lines in which the ER is expressed from a vector introduced into the cell.

Where a cell line expressing the estrogen receptor is used a reporter gene construct comprising an ERE operably linked to a reporter gene may be introduced into the cell together with a cyclin D1 expression vector. Two or more EREs (for example 3, 4 or 5) may be present in the construct and this may enhance sensitivity of the assay. The reporter gene may be any suitable reporter gene used in the art. Such reporter genes include chloramphenicol acetyl transferase (CAT) or luciferase. The cyclin D1 expression vector will comprise DNA encoding cyclin operably linked to a promoter capable of expressing the gene in the host cell. Suitable promoters include viral promoters such as a CMV or SV40 promoter.

The cell lines used in assays of the invention may be used to achieve transient expression of the cyclin although in a further aspect of the invention cells which are stably transfected with constructs which express the cyclin gene and, where required, the ER may also be generated. Means to generated stably transformed cell lines are well known in the art and such means may be used here.

Suitable cell lines include breast cancer cell lines which are widely available in the art. The Examples which follow utilise the T47D breast cancer cell line although other suitable Examples include MCF-7 and MDA.

Where the cell line does not express ER, a construct capable of expressing this protein may also be introduced into the cell operably linked to a suitable promoter.

The precise format of the assays of the invention may be varied by those of skill in the art using routine skill and knowledge. In the in vitro assays of the invention, the amount of cyclin D1 and estrogen receptor may be varied depending upon the scale of the assay. In general, the person of skill in the art will select relatively equimolar amounts of the two components, say from 1:10 to 100:1, preferably from 1:1 to 10:1, molar ratio of cyclin D1 to ER. However there may be particluar assay formats which can be practiced outside this range. In the in vivo assays of the invention, it will be desirable to achieve sufficient expression of cyclin D1 to recruit sufficient ER to an ERE such that the effect of a putative inhibitor compound may be measured. Where the cell does not express ER, sufficient expression of this will also be required. The level of expression of cyclin D1 (and where necessary ER) may be varied within fairly wide limits, so that the intracellular levels of the two may vary by a wide ratio, for example from 1:10 to 1000:1, preferably 1:1 to 100:1, molar ratio of cyclin D1 to ER.

The amount of putative inhibitor compound which may be added to an assay of the invention will normally be determined by trial and error depending upon the type of compound used. Typically, from about 0.01 to 100 nM concentrations of putative inhibitor compound may be used, for example from 0.1 to 10 nM.

Inhibitor compounds which may be used may be natural or synthetic chemical compounds used in drug screening programmes. Extracts of plants which contain several characterised or uncharacterised components may also be used. A further class of putative inhibitor compounds can be derived from the cyclin D1 and ER protein sequences. Peptide fragments of from 5 to 40 amino acids, for example from 6 to 10 amino acids from the region of cyclin D1 and ER which are responsible for the interaction between these proteins may be tested for their ability to disrupt this interaction. Antibodies directed to the site of interaction in either protein form a further class of putative inhibitor compounds. Candidate inhibitor antibodies may be characterised and their binding regions determined to provide single chain antibodies and fragments thereof which are responsible for disrupting the interaction between cyclin D1 and estrogen receptor.

Other candidate inhibitor compounds may be based on modelling the 3-dimensional structure of cyclin D1 and ER and using rational drug design to provide potential inhibitor compounds with particular molecular shape, size and charge characteristics.

Candidate inhibitor compounds obtained according to the method of the invention may be prepared as a pharmaceutical preparation. Such preparations will comprise the compound together with suitable carriers, diluents and exipients. Such formulations form a further aspect of the present invention. The formulations may be used in methods of treatment of proliferative diseases, particularly those involving cells which grow in response to stimulation by estrogen, for example breast cancer.

Candidate inhibitor compounds may also be used in combination with any other anti-proliferative compounds used to treat hyperproliferative diseases such as cancers. In such a case, the assay of the invention, when conducted in vivo, need not measure the degree of inhibition of binding or transcriptional activation caused by the inhibitor compound being tested. Instead the effect on cell growth or proliferation may be measured. It may be that such a modified assay is run in parallel or subsequent to the main assay of the invention in order to confirm that any effect on cell growth or proliferation is as a result of the inhibition of binding or transcriptional activation caused by said inhibitor compound and not merely a general toxic effect.

A preferred class of such compounds are anti-estrogens such as tamoxifens, eg. 4-hydroxytamoxifen, or pure anti-estrogens such as N-(n-butyl)-11-[3,17beta-dihydroxy-estra-1,3,5(10)-trien-7 alpha-yl]N-methylundecanamide, known as ICI 164,384. Such anti-estrogen compounds may be included in the assay in order to determine inhibitor compounds which may act additively or synergistically with anti-estrogens. This will facilitate the provision of combination therapy against estrogen-responsive tumours.

Estrogen responsive tumours are primarily breast tumours although other tumour types which have been found to be estrogen-responsive include endometrial cancer and ovarian carcinoma.

The interaction between cyclin D1 and the ER may also be used to monitor the status and progress of disease states associated with enhanced transcription of ERE regulated genes. For example, antibodies may be generated which bind to the cyclin/ER complex or to one or other component in the allosteric form induced by binding to the other. Such antibodies may be raised in routine ways, using as immunogen the cyclin/ER complex which may be stabilized by using protein cross-linking reagents. The antibodies generated by such an immunogen may be screened against the immunogen and separately against the cyclin and ER, in order to obtain antibodies which recognise only the proteins when complexed. Such antibodies may be packaged in kits with other suitable reagents for immunodiagnosis and used in the clinic to monitor disease states.

The following Examples illustrate the invention.

D-type cyclins are strongly implicated in controlling transition through the $G_1$ phase of the cell cycle. Three closely related human D-type cyclins have been identified,[1,2], which all interact with and activate cyclin dependent kinases (CDK) 4 and 6, although they have specialized functions in distinct cell types [3,4]. It has been shown recently that cyclin D1 deficient mice have a defect in proliferation of the estrogen-responsive breast epithelium during pregnancy [5,6]. This, together with the frequent amplification of the cyclin D1 gene in human breast cancer, suggests a critical role for both estrogens and cyclin D1 in proliferation and differentiation of breast epithelium. Here we report that cyclin D1 interacts directly with the estrogen receptor and potentiates transcription of estrogen receptor-regulated genes. Our data indicate that this effect is not the result of a phosphorylation of estrogen receptor by cyclin D1/CDK complexes and is independent of ligand binding to the receptor. Therefore, these results highlight a novel role for cyclin D1 in growth regulation of estrogen-responsive tissues.

The estrogen receptor (ER), which belongs to the conserved family of steroid and thyroid receptors, is a 66 kilodalton nuclear regulatory protein that functions as a hormone-activated transcription factor. Receptor activation is thought to be a consequence of ligand-induced conformational changes in the structure of the ER [7,8]. The estrogen-ER complex binds with high affinity to a well-defined 13-basepair palindromic sequence, the estrogen response element (ERE), which is usually located upstream of an estrogen-responsive gene [7,9,10]. Activation of ERE-containing genes is elicited in ER-positive cells by treatment with 17β-estradiol and can be measured by a chloramphenicol acetyl transferase (CAT) reporter gene with an upstream ERE site in these cells [11,12]. Using this system, we have investigated the effect of cyclin D1 in combination with its associated kinase CDK4 on ERE-responsive transcription in the well-differentiated and estrogen-responsive T47D breast cancer cell line. FIG. 1 shows that cyclin D1 is a strong enhancer of ERE-responsive gene transcription in the presence of 17β-estradiol. The activity of the ERE-containing reporter gene increased with increasing amounts of cyclin D1 expression vector. Up to sevenfold potentiation was seen as compared to its basal level of 17β-estradiol-activated transcription, which was arbitrarily set at 1 (FIG. 1a). The importance of the ERE in this effect is supported by the fact that cyclin D1 did not stimulate the activity of a reporter gene that lacked an ERE (FIG. 2a).

Figure 1D:
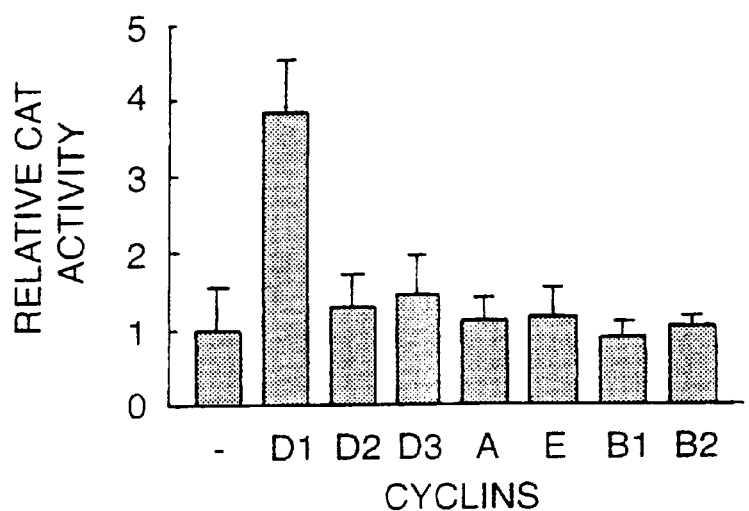
Figure 2A:
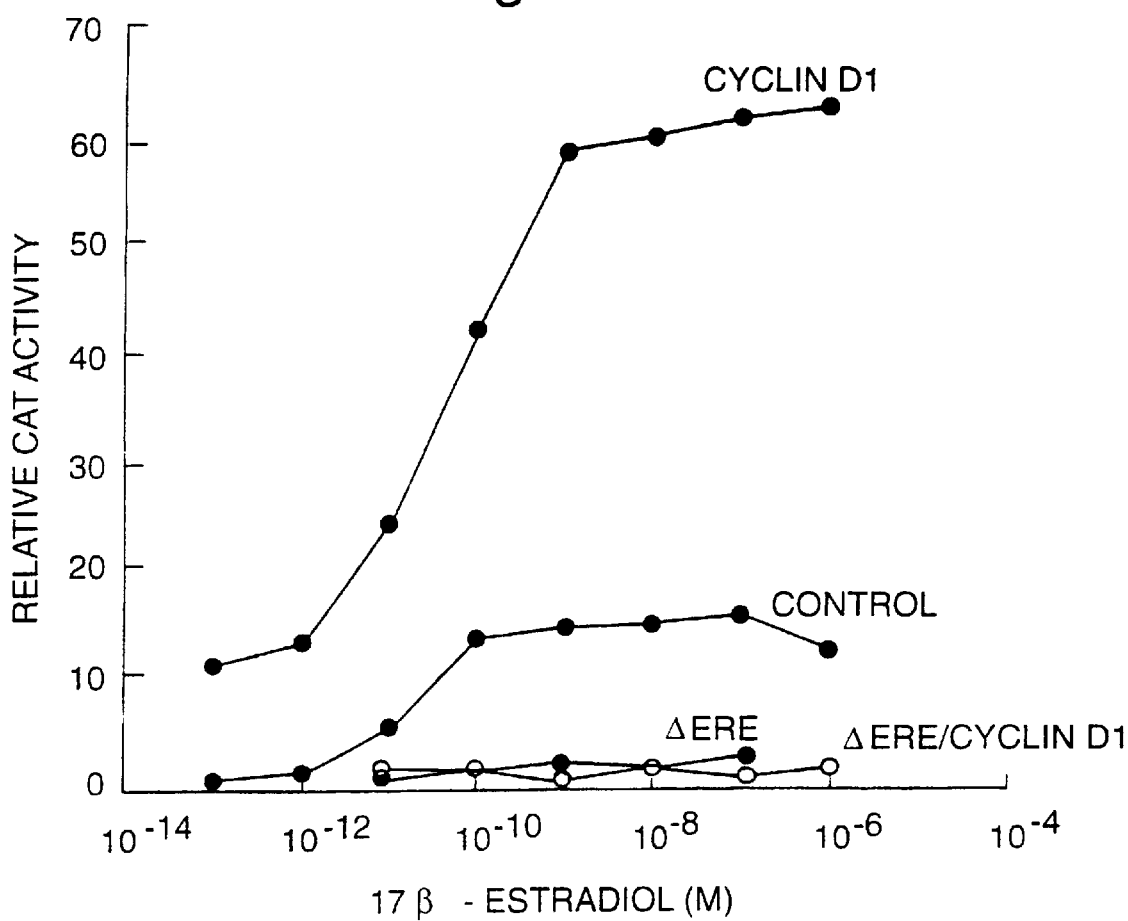
FIGS. 2A–2C show cyclin D1 enhances ERE responsive gene transcription independently of ligand activation of ER.

Striking was that cyclin D1 in combination with its kinase partner CDK4 did not enhance transcription of ERE-CAT, nor did CDK4 alone (FIG. 1b). To verify that a CDK was not required in this process, a mutant of cyclin D1 (cyclin D1-KE) was used, which carries a mutation in the cyclin box and fails to bind to CDKs [13]. Like wild type cyclin D1, the cyclin D1-KE mutant potentiated transcriptional activation of ER in a dose-dependent manner. Cotransfection of CDK4 and cyclin D1-KE did not influence the cyclin D1 effect on transactivation (FIG. 1b). The binding of cyclin D1 to CDKs without associated kinase activity, such as the dominant negative CDK4 mutant (CDK4 DN) and CDK2 [14], prevented the stimulatory effect of cyclin D1, whereas a CDK which cannot bind to cyclin D1, CDC-2, was ineffective (FIG. 1b). This suggests that the kinase activity of any cyclin D1-CDK complex is irrelevant in activating ERE-mediated transcription. Significantly, cotransfection of cyclin D1 and CDK4 with p16$^{INK4}$, a CDK inhibitor which competes with cyclin D1 for binding to CDK4[15], enhanced transcription to a level comparable with that induced by cyclin D1 alone (FIG. 1c). Taken together, these data indicate that 'free' cyclin D1 can enhance ERE-mediated transcription, whereas CDK-bound cyclin D1 is inactive. To investigate whether the motif in cyclin D1 that mediates binding to the retinoblastoma protein (pRB) was required for this process, another cyclin D1 mutant (cyclin D1-GH) was used. Cyclin D1-GH carries a mutation in the LXCXE motif and this mutation renders the protein unable to bind to pocket proteins, such as pRB [13,16]. FIG. 1a shows that this cyclin D1 mutant enhanced the expression of the ERE-CAT reporter gene to the same extent as wild type cyclin D1, indicating that this enhancement of transcription was independent of an intact pRB-binding motif in cyclin D1.

Figure 1E:
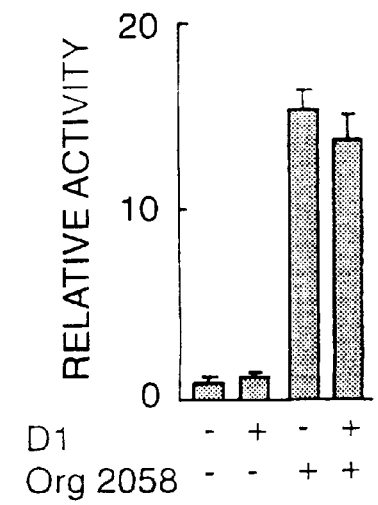

The uniqueness of cyclin D1 among the cyclins in the activation of ERE-mediated transcription is illustrated in FIG. 1 d/e. Cyclin D1 potentiated ER-mediated transcription, whereas the other D type cyclins (which were expressed at comparable levels, data not shown) and cyclin A, cyclin E, cyclin B1 and cyclin B2 did not. To study whether cyclin D1 activates transcription mediated by other steroid receptors, we tested the effect of cyclin D1 on the progesterone receptor using a progesterone response element (PRE) containing a reporter gene construct (FIG. 1e). As expected, transcription of the PRE-reporter gene was induced by a progestin, Org 2058. However, cyclin D1 failed to enhance PRE-mediated transcription both in the presence and absence of Org 2058. Thus, cyclin D1-mediated activation is not general among steroid receptors.

Figure 2B:
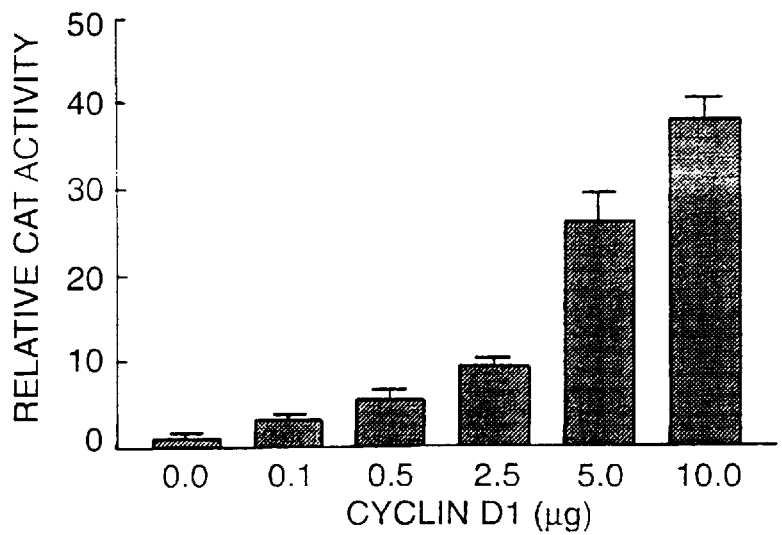
Figure 2C:
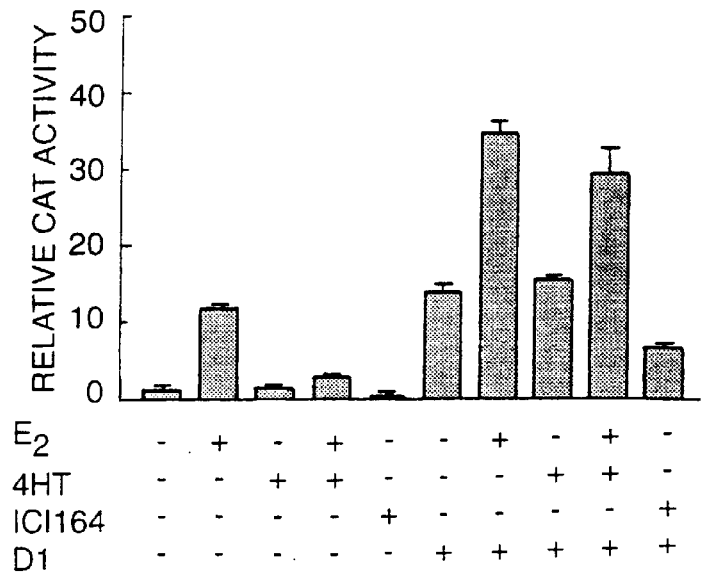

To study the contribution of estrogen in the observed enhanced transcription of ERE-responsive genes by cyclin D1, T47D cells were transiently transfected with cyclin D1 and the ERE-reporter construct and were maintained in medium with various concentrations of 17β-estradiol. FIG. 2a demonstrates that the activity of the ERE-CAT reporter gene was dramatically enhanced in T47D cells by 17β-estradiol, as expected. However, the activity of the ERE-CAT reporter gene was enhanced substantially by cotransfection of cyclin D1 expression vector at all concentrations of 17β-estradiol tested. In the absence of ligand, cyclin D1 was able to restore the transcriptional activity to levels similar or even higher than obtained with 17β-estradiol (0.1 nM) alone (FIG. 2b). These data indicate that cyclin D1 and estrogen are synergistic in stimulating estrogen-regulated transcription and that cyclin D1 can also act independently of estrogen in activating ERE-responsive transcription. Therefore, cyclin D1 can substitute for estrogen in activating ER. This may contribute to the mitogen-independent proliferation in cyclin D1 overexpressing cells, which is frequently found in breast tumours [17-19]. A hormone-independent mechanism of action of cyclin D1 is further supported by experiments with the anti-estrogen 4-hydroxytamoxifen, which binds to the estrogen receptor in a manner that is competitive with estrogen, but fails to activate gene transcription [20]. FIG. 2c shows that 4-hydroxytamoxifen antagonized the effect of 17β-estradiol on transcriptional activation, but did not prevent transcriptional potentiation by cyclin D1. Also a pure anti-estrogen ICI 164,384, which blocks both activation functions of ER (AF-1 and AF-2), did not prevent cyclin D1 transactivation. These data indicate that cyclin D1 was effective in activating transcription of ERE-containing genes in cells harbouring ERs occupied with 17β-estradiol as well as in cells with unliganded ERs.

Figure 3A:
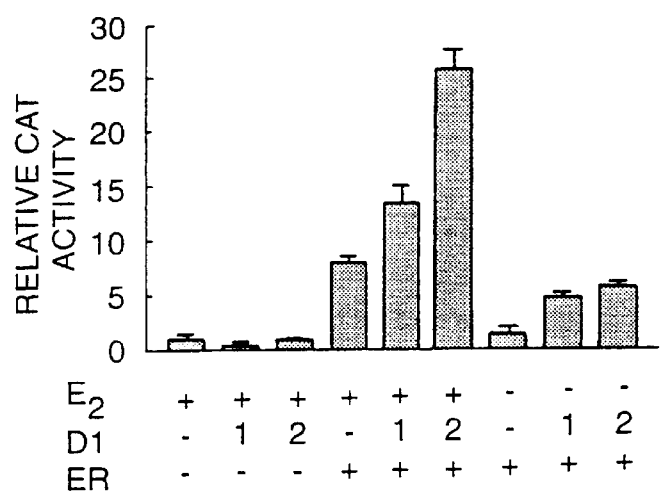
FIGS. 3A–3C show the potentiation of gene activation by cyclin D1 is ER-mediated.
Figure 3B:
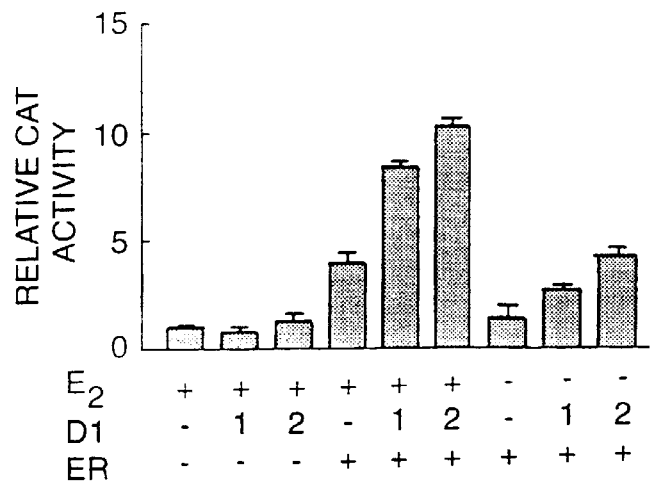
Figure 3C:
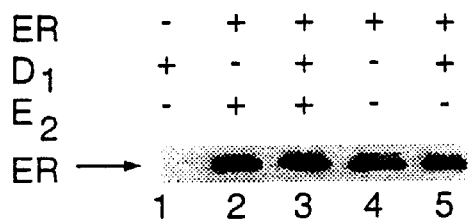

Because estrogen was not required for this cyclin D1 action, the question arose whether ER itself was required for the effect of cyclin D1 on ERE-responsive transcription. Therefore, we used the human osteosarcoma cell line U2-OS and cervical carcinoma cell line HeLa, which both have negligible levels of ER. Cotransfection of cyclin D1 and the ERE-reporter gene construct in these cells did not increase ERE-responsive transcription, whereas cotransfection of these genes with a human ER expression vector led to activation of the ERE-CAT (FIGS. 3a and b). As in T47D cells, cyclin D1 stimulated transcription both in the presence and in the absence of 17β-estradiol in ER-transfected cells. Thus, cyclin D1 acts through the ER to enhance transcription of ERE-containing genes. The ER protein levels in U2-OS cells containing ectopicly expressed cyclin D1 were similar to those seen in cells without ectopic cyclin D1 (FIG. 3c). Therefore, the enhancement of ERE-responsive gene transcription by cyclin D1 was not due to a modulation of ER protein levels.

Figure 4B:
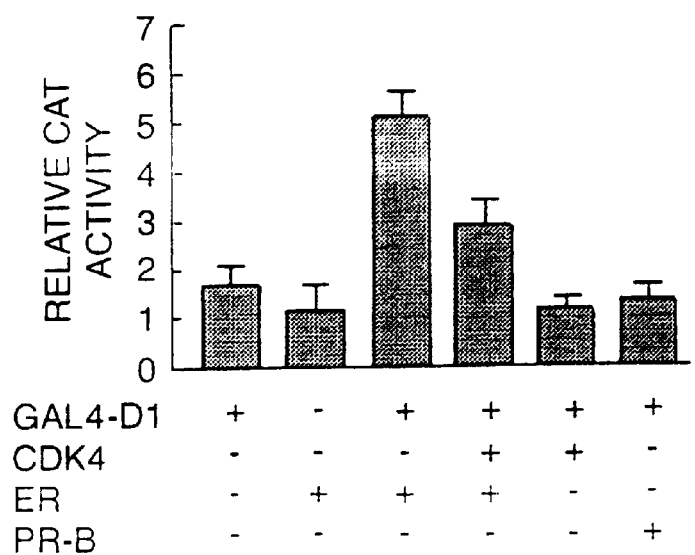
Figure 4C:
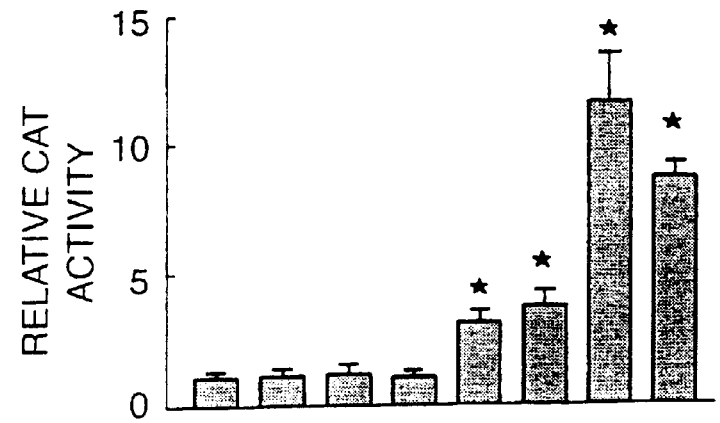

Cyclin D1 could well activate ER-mediated transcription through direct binding to ER. When we mixed in vitro translated $^{35}$S-methionine labelled human ER with GST-cyclin D1 protein in an in vitro binding assay, we did indeed observe specific binding of ER to GST-cyclin D1 (FIG. 4a). Binding was observed both with liganded as well as with unliganded receptor (lanes 2 and 3). To investigate whether cyclin D1 also binds to both liganded ER and unliganded ER in vivo, we used a mammalian two hybrid assay. To test the in vivo binding between cyclin D1 and liganded ER, a chimeric expression vector harbouring cyclin D1 fused to a GAL4 DNA binding domain (GAL4-D1) was generated and cotransfected with ER and a GAL4-site containing reporter plasmid into U2-OS cells. Transcription of the reporter gene should be stimulated in the presence of 17β-estradiol if a complex is formed between GAL4-D1 and ER, where the transactivational activity in this complex is provided by the hormone-dependent activation domain AF2 in ER. As is shown in FIG. 4b, GAL4-dependent CAT transcription was minimally stimulated when either GAL4-D1 or ER were transfected separately. However, CAT activity was significantly increased by GAL4-D1 in combination with ER suggesting a direct interaction in vivo between cyclin D1 and liganded ER. Consistent with the data obtained in the ERE-CAT assays (FIG. 1), CDK4 and progesterone receptor (PR-B) act in this in vivo binding assay as a competitor and as a negative control, respectively. To investigate an in vivo binding between cyclin D1 and unliganded ER, we next have generated a ER fusion protein containing a herpes simplex virus VP16 activation domain (VP16-ER). Cotransfection of two chimeric expression vectors, GAL4-D1 and VP16-ER, in combination with a GAL4-dependent reporter construct resulted in a significant increase in transcription of the reporter gene (FIG. 4c). To investigate whether cyclin D1 only acts on ER specifically bound to an ERE sequence, we used an ER fused to GAL4 DNA binding domain in a GAL4-dependent reporter system. Also in this assay, cyclin D1 enhanced GAL4-dependent transcription in a ligand independent manner (FIG. 4d), indicating that cyclin D1 does not require sequence-specific DNA binding of ER for activation. Taken together, these results indicate that cyclin D1 interacts directly both with liganded and unliganded ER in vivo and can regulate ER-mediated transcription through protein-protein interactions.

To get an impression of the relative strength of the ER/cyclin D1 and cyclin D1/CDK4 interactions, we have performed transfection studies with GAL4-D1 in combination with VP16-CDK4 (FIG. 4c). Using the mammalian two hybrid system, the relative activity of GAL4-D1/VP16-CDK4 was three fold increased as compared with GAL4-D1/VP16-ER. This suggests that, besides the binding of cyclin D1 to its kinase partner CDK4, the cyclin D1-ER interaction is of physiological importance.

Immunoprecipitation studies support the in vivo interaction between cyclin D1 and (un)liganded ER. HA-tagged ER constructs were transfected together with cyclin D1 into U2-OS cells and maintained in 17β-estradiol enriched or free conditions. HA-ER fusion protein was immunoprecipitated using an antibody against HA-epitope tag (12CAS) and analyzed for cyclin D1 binding by Western blot analysis. Cotransfection with cyclin D1 resulted in coimmunoprecipitation of cyclin D1 with liganded as well as with unliganded ER. Thus, cyclin D1 physically interacts both with liganded and unliganded ER in vivo.

Figure 5:
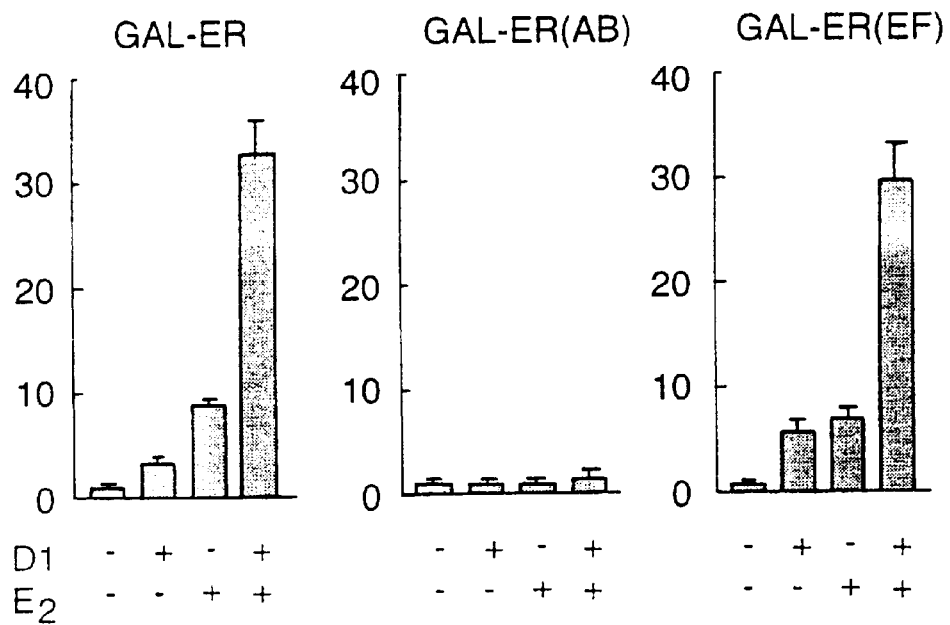
FIG. 5 shows that activation of ER by cyclin D1 does not require sequence specific DNA binding and cyclin D1 specifically activates the EF region of ER.

In order to localize the ER domain which responds to cyclin D1, we have used chimeras in which either regions A/B (amino acids 1–184) or E/F (amino acids 282–595) were fused to the GAL4 DNA binding domain, yielding GAL-ER(AB) (Ali et al., 1993) and GAL-ER(EF) (Webster et al., 1988). Using these constructs in a GAL4-dependent reporter system in combination with cyclin D1, we found that the GAL-ER(AB) construct did not respond to cyclin D1 (FIG. 5). In contrast, cyclin D1 was able to stimulate transactivation by both GAL-ER(EF) and GAL-ER wild type to the same extent (FIG. 5). To ask whether cyclin D1 mediated transactivation of ER correlated with binding to ER, we performed transient transfection experiments. Immunoprecipitation of GAL fusion proteins, which contain the AB- or EF region of ER, from transiently transfected U2-OS cell extracts, followed by western blot analysis using a monoclonal antibody directed against cyclin D1 revealed that cyclin D1 predominantly binds to the EF region and not, or at least with lower affinity, to the AB region of ER. This binding between cyclin D1 and the C-terminal domain of ER occurred both in the presence as well as in the absence of 17β-estradiol. The interaction between the carboxyterminal region of ER and cyclin D1 was also confirmed in a GST pulldown experiment using bacterially produced and purified His-cyclin D1 and GST-ER(EF), containing amino acids 340–595. Since no other mammalian proteins were present in this experiment, these data indicate that cyclin D1 acts through direct binding to the C-terminal EF region of ER.

To investigate whether the cyclin D1 action on transcription was due to enhanced ER binding to ERE, we analyzed the binding of ER-ERE complexes in response to cyclin D1 using a gel retardation assay. When transiently transfected into U2-OS cells and maintained in 17β-estradiol enriched medium, cyclin D1 increased the ER binding to ERE sequence 3-fold. Consistent with data obtained from ERE-CAT and interaction assays, cyclin D1 in combination with CDK4 was less effective in stimulating ER binding to ERE sequence. Analysis of DNA binding complexes in response to hormone deprivation revealed that cyclin D1 stimulated ER binding to ERE, which was absent in cells lacking ectopic cyclin D1. Antibody supershift experiments of ERE-associated complexes revealed that ER is present in these ERE-associated complexes. Thus, cyclin D1 triggers binding of liganded and unliganded ER to ERE sequences. To investigate whether cyclin D1 only acts on ER specifically bound to an ERE sequence, we used an ER fused to GAL4 DNA binding domain in a GAL4-dependent reporter system. In this assay, cyclin D1 enhanced GAL4-dependent transcription in a ligand independent manner (FIG. 5), indicating that cyclin D1 does not require sequence-specific DNA binding by ER for activation. These data therefore indicate that cyclin D1 also affects ER activity by enhancing transactivation by ER. In conclusion, cyclin D1 acts by both enhancing the DNA binding and transactivation capacity of ER.

The present study establishes a new role for cyclin D1 as a positive regulator of ER-mediated transcription through a direct interaction with ER. Our data suggest that cyclin D1 is involved in activation of ERE-containing genes both in the presence and absence of estrogen. Cyclin D1 may therefore contribute to stimulation of estrogen-mediated cell proliferation in hormone-responsive tissues, such as breast epithelium. Consistent with this is the recent finding that cyclin D1 deficient mice have a defect in hormone-responsive proliferation of breast epithelium [5,6]. Cyclin D1 can also enhance transcription of ER-responsive genes without the assistance of estrogens, providing a mechanism for estrogen-independent growth of cyclin D1 overexpressing breast tumour cells.

The materials and methods used in this example are provided in more detail below in relation to the following detailed description of the drawings.

FIG. 1.

Cyclin D1 potentiates ERE responsive gene transcription in the presence of 17β-estradiol.

a. The effect of cyclin D1 and its associated kinase activity on ERE-mediated transcription. b. The effects of CDKs on regulation of ERE-mediated transcription by cyclin D1. c. The effect of p16$^{INK4}$ in ectopic cyclin D1/CDK4 expressing cells on ERE-mediated transcription.

d. The specificity of cyclin D1 in activation of ERE-mediated transcription. e. The effect of cyclin D1 on PRE-mediated transcription.

An ERE/PRE-reporter construct was used in transient transfections of T47D breast cancer cells [11,12] together with wild type cyclins, CDKs and p16$^{INK4}$ expression vectors, or with mutants of cyclin D1, which are unable to bind to CDK4 (cyclin D1-KE) or with retinoblastoma protein pRb (cyclin D1-GH) or a catalytic inactive mutant of CDK4 (CDK4-DN).

METHODS. The reporter plasmids, ERE-TK-CAT (3 μg) containing the ERE from the vitellogenin A2 gene or (PRE)$_2$-TK-luc, were transfected transiently into subconfluent T47D cells using the calcium phosphate precipitation technique 21. The expression vectors used in the transient transfection studies were pCMV cyclin D1, cyclin D2, cyclin D3, cyclin A, cyclin E, cyclin B1, cyclin B2, CDC2, CDK2, CDK4, CDK4-DN, cyclin D1-GH and cyclin D1-KE, which have been described elsewhere [13,22]. For panel 1b, 1d and 1e, the amounts of these expression vectors was 2.5 μg per 10 cm dish. In panel 1c, 1 μg cyclin D1 and CDK4 expression vectors was used and for p16$^{INK4}$ the amount was variable: 1=0.5 μg; 2=1.0 μg; 3=5.0 μg. pCMV-luciferase (panel 1a–1d, 0.5 μg) or pCMV-β galactosidase (panel 1e, 0.5 μg) served as an internal control. During the transfection, cells were maintained in phenol red free Dulbecco's Minimal Essential Medium (DMEM) containing 1 nM ligand (the estrogen 17β-estradiol for panels 1a–1d and the progestin Org 2058 for panel 1e). After 40 h, cells were harvested and resuspended in 0.1 M Tris-HCl pH 8.0 and assayed for luciferase activity (Promega, Luciferase system), β-galacosidase activity (Tropix, galactolight assay) and/or CAT activity [23]. In panels 1a to 1d, the relative CAT activity was calculated by normalizing to the luciferase activity and divided by the ERE-CAT activity in the presence of 17β-estradiol (1 nM); in panel 1e the relative activity was calculated by normalizing to β-galactosidase and was divide by the basal transcription in the absence of ligand.

FIG. 2.

Cyclin D1 enhances ERE responsive gene transcription independently of ligand activation of ER.

a. The effect of estrogen and cyclin D1 on ERE responsive transcription activity.T47D cells were maintained in medium containing various concentrations of 17β-estradiol and were transfected with an ERE-reporter construct or a reporter construct that lacked ERE (‚ERE) in concert with cyclin D1 expression vector. b. Cyclin D1 activates ERE-CAT transcription in 17β-estradiol free conditions. T47D cells were transfected with various amounts of cyclin D1 constructs in the absence of ligand. c. Cyclin D1 induces ERE-gene expression by a hormone-independent mechanism. The effect of cyclin D1 on ERE-responsive transcription was examined in T47D cells treated with 17β-estradiol and/or the antiestrogens 4-hydroxytamoxifen and ICI 164, 384.

METHODS. T47D cells were transfected with ERE-reporter plasmid, cyclin D1 expression vector and the internal control pCMV-luciferase construct as described in Experimental Procedures. The amount of cyclin D1 plasmid used for transient transfections was 5 μg per 10 cm plate in panel A/C and variable in panel B. During the experiment, cells were maintained in phenol red free DMEM supplemented with insulin (10 μg/ml) and transferrin (10 μg/ml); cells were treated with 17β-estradiol (0.1 nM) and/or anti-estrogen (100 nM) as indicated. After 40 h, cells were lysed and assayed for both CAT activity and luciferase activity (Promega, Luciferase system) Data are expressed as relative CAT activity compared with basal CAT level in the absence of 17β-estradiol. E2, 17β-estradiol; D1, cyclin D1; 4HT, trans-4-hydroxytamoxifen; ΔERE, pCAT lacking ERE.

FIG. 3.

The potentiation of gene activation by cyclin D1 is ER-mediated.

a. ER is involved in modulation of ERE-responsive gene transcription triggered by cyclin D1.

The human ER-negative U2-OS and HeLa cell lines were used to investigate the role of ER in potentiation of ERE-CAT transcription activity by cyclin D1. Together with ERE-CAT and pCMV-luciferase plasmids, cells were transfected with cyclin D1 in combination with human ER and tested for transcription of the CAT reporter gene. b. Cyclin D1 does not moaulate ER protein synthesis. U2-OS cells transfected with ER and/or cyclin D1 were subjected to immunoblotting using an antibody directed against ER.

METHODS. Transient transfections. Cells were transfected with 0.4 μg human ER construct (HEGO [24]; and cyclin D1 construct (0.25 μg or 1 μg) together with 3 μg ERE-CAT reporter construct and 0.5 μg pCMV luciferase as internal control as described in FIG. 1. Cells were maintained in phenol red free DMEM containing insulin/transferrin (10 μg/ml each) or the ligand 17β-estradiol (1 nM). After transfection, cells were lysed and assayed for both CAT and luciferase activity. The CAT activity was normalized to luciferase activity and divided by the basal CAT activity of cells lacking ER in order to obtain the "relative CAT activity" as indicated. Western blotting. U2-OS cells, transfected with ER (0.4 μg) together with cyclin D1 (1 μg), were lysed in extraction buffer (50 mM Tris pH 7.4, 150 mM KCl, 15 mM NaCl, 30 mM MgCl2, 10 mM EGTA, 0.5% NP-40, 1 mM PMSF, 5 μg/ml aprotinin, 10 μg/ml trypsin inhibitor, 10 μg/ml leupeptin). Equal amounts of total cell extracts were separated by SDS-polyacrylamide gel electrophoresis and blotted to a cellulose nitrate membrane. Immunoblot analysis was performed with anti-cyclin D1 (DCS-6, Progen) and anti-ER (LH2, Novacastra) monoclonal antibodies and immunodetection was performed using the enhanced chemiluminiscence system. E$_2$, 17β-estradiol; D1, cyclin D1: 1=0.25 μg, 2=1.0 μg; ER, estrogen receptor.

FIG. 4.

Cyclin D1 interacts with (un)liganded ER.

a. The in vitro interaction between cyclin D1 and ER. The in vitro interaction between cyclin D1 fused to glutathionestransferase (GST) and $^{35}$S-labeled ER was studied both in the presence and absence of 17β-estradiol. GST-cyclin D1 or control GST protein were mixed with $^{35}$S-labeled ER and immobilized on glutathion-agarose beads to establish in vitro binding. Lane 1 represents 10% of ER input, lanes 2 and 3 represent the amount of ER bound to GST-cyclin D1 and lanes 4 and 5 represent the amount of ER bound to GST protein. b. The in vivo interaction between cyclin D1 and ER in the presence of 17β-estradiol. The in vivo interaction between cyclin D1 and liganded ER was studied using a mammalian two hybrid assay with a chimeric protein GAL4-D1, which contains the GAL4 DNA binding domain (amino acid 1-147) fused to cyclin D1, in combination with ER which acts as a hormone-activated transcription factor. As a result of proteinprotein interaction, hybrid proteins are able to stimulate transcription of a GAL4-dependent reporter construct (G5BCAT). This reporter gene construct, G5BCAT, contains five GAL4 binding sites 5' to the E1B TATA sequence $^{25}$. The human steroid progesterone receptor (PR-B) served as negative control. The unliganded ER also did not stimulate CAT transcription. GAL4-D1 in combination with VP16-CDK4 and dimerized ER served as positive controls. The results are expressed as average of at least three separate experiments ± SD and related to CAT activity of a transfection using vector containing GAL4 DNA binding domain in combination of GSBCAT reporter vector in the presence of 10 nM ligand (17β-estradiol or Org 2058) for panel B and in the absence of ligand for panel C. $E_2$, 17β-estradiol; D1, cyclin D1; ER, estrogen receptor; *P≦0.05.

METHODS. In vitro binding assay. Total bacterial extracts expressing cyclin D1 protein fused to glutathione-S-transferase (GST) or GST protein alone were generated and purified on gluthathione agarose beads. $^{35}$S-methionine labeled ER protein was prepared by in vitro transcription/translation and incubated with 1 μg GST-cyclin D1 in ELB (250 mM NaCl, 0.1% NP-40, 50 mM Hepes pH 7.0, 5 mM EDTA) with 0.5 mM DTT, 1 mM PMSF, 10 μg/ml aprotinin and 10 μg/ml leupeptin, bound to gluthathione-agarose beads, washed in ELB, eluted and fractionated by SDS-polyacrylamide gel electrophoresis. GAL4-dependent reporter system. Generating chimeric proteins, the full length cyclin D1 or ER cDNAs were inserted in frame downstream of the GAL4 (1–147) DNA binding domain fragment and sequence coding for the acidic activation domain of the Herpes Simplex virus VP16 protein. U2-OS cells were transfected in panel b with 1.5 μg GAL4-D1, ER, PR-B and CDK4 expression vectors in combination with 10 μg GSB-CAT reporter constructs, whereas 5 μg of the indicated constructs was used in panels c and d. As an internal control, 0.5 μg of pCMV-luciferase plasmid was used in the assays. The CAT activity was corrected for differences in transfection efficiency by normalizing to luciferase activity. The results are expressed as average of at least three separate experiments ±SD and related to CAT activity of a transfection using vector containing GAL4 DNA binding domain in combination of G5BCAT reporter vector in the presence of 1 nM ligand (17β-estradiol or Org 2058) for panels b/c and in the absence of ligand for panel d. $E_2$, 17β-estradiol; D1, cyclin D1; ER, estrogen receptor; *P≦0.05.

FIG. 5

Activation of ER by cyclin D1 does not require sequence-specific DNA binding and cyclin D1 specifically activates the EF region of ER.

U2-OS cells were transfected with 1,5 μg of a vector encoding full length ER, AB region of ER or EF region of ER fused to GAL4 DNA binding domain yielding GAL-ER, GAL-ER(AB) and GAL-ER(EF), respectively. Transfection studies were performed together with cyclin D1 expression vector (1,5 μg) and G5BCAT reporter vector (3 μg) and cells were kept in the presence or absence of 10 nM 17β-estradiol. The results are expressed as relative CAT activity compared with basal CAT level in the absence of ligand.

REFERENCES

1. Inaba, T., Matsushime, H., Valentine, M., Roussel, M. F., Sherr, C. J. & Look, A. T. *Genomics* 13, 565–574 (1992).
2. Xiong, Y., Menninger, J., Beach, D. & Ward, D. C. *Genomics* 13, 575–584 (1992).
3. Matsushime, H., Roussel, M. F., Ashmun, R. A. & Sherr, C. J. *Cell* 65, 701–713 (1991).
4. Motokura, T., Keyomarsi, K., Kronenberg, H. M. & Arnold, A. *J Biol Chem* 267, 20412–20415 (1992).
5. Sicinski, P., Donaher, J. L., Parker, S. B., et al. *Cell* 82, 621–630 (1995).
6. Fantl, V., Stamp, G., Andrews, A., Rosewell, I. & Dickson, C. *Genes & Development* 9, 2364–2372 (1995).
7. Kumar, V. & Chambon, P. *Cell* 55, 145–156 (1988).
8. Tsai, S. Y., Carlstedt-Duke, J., Weigel, N. L., et al. *Cell* 55, 361–369 (1988).
9. Evans, R. M. *Science* 240, 889–895 (1988).
10. Beato, M. *Cell* 56, 335–344 (1989).
11. Klein-Hitpass, L., Ryffel, G. U., Heitlinger, E. & Cato, A. C. *Nucleic Acids Res* 16, 647–663 (1988).
12. Klein-Hitpass, L., Schorpp, M., Wagner, U. & Ryffel, G. U. *Cell* 46, 1053–1061 (1986).
13. Hinds, P. W., Dowdy, S. F., Eaton, E. N., Arnold, A. & Weinberg, R. A. *Proceedings of the National Academy of Sciences of the United States of America* 91, 709–713 (1994).
14. Ewen, M. E., Sluss, K. H., Sherr, C. J., Matsushime, H., Kato, J. & Livingston, D. M. *Cell* 73, 487–497 (1993).
15. Parry, D., Bates, S., Mann, D. J. & Peters, G. *EMBO J* 14, 503–511 (1995).
16. Dowdy, S. F., Hinds, P. W., Louie, K., Reed, S. I., Arnold, A. & Weinberg, R. A. *Cell* 73, 499–511 (1993).
17. Schuuring, E., Verhoeven, E., Mooi, W. J. & Michalides, R. J. *Oncogene* 7, 355–361 (1992).
18. Bartkova, J., Lukas, J., Muller, H., Lutzhoft, D., Strauss, M. & Bartek, J. *Int J Cancer* 57, 353–361 (1994).
19. Michalides, R. J., Van Veelen, N., Hart, A., Loftus, B., Wientjens, E. & Balm, A. *Cancer Res* 55, 975–978 (1995).
20. Berry, M., Metzger, D. & Chambon, P. *EMBO J* 9, 2811–2818 (1990).
21. Graham, F. L. & Eb, A. J. *Virology* 52, 456–467 (1973).
22. Hinds, P. W., Mittnacht, S., Dulic, V., Arnold, A., Reed, S. I. & Weinberg, R. A. *Cell* 70, 993–1006 (1992).
23. Seed, B. & Sheen, J. Y. *Gene* 67, 271–277 (1988).
24. Migliaccio, A., Castoria, G., de Falco, A., et al. *J Steroid Biochem Mol Biol* 38, 407–413 (1991).
25. Kim, S. J., Onwuta, U. S., Lee, Y. I., Li, R., Botchan, M. R. & Robbins, P. D. *Mol Cell Biol* 12, 2455–2463 (1992).

We claim:

1. An assay for an inhibitor of estrogen responsive tumour cells which comprises:
    a) bringing into contact a cyclin D1, an estrogen receptor and a putative inhibitor compound under conditions where the cyclin and the estrogen receptor, in the absence of inhibitor, are capable of forming a complex which is capable of binding to an estrogen response element;
    b) providing an estrogen response element to which the complex is capable of binding and transcriptionally activating; and
    c) measuring the degree of inhibition of binding or transcriptional activation caused by said inhibitor compound.

2. An assay according to claim 1 wherein the cyclin and the estrogen receptor are fused to separate functional DNA binding domains of a transcription factor.

3. An assay according to claim 1 or 2 which is performed in vivo in an estrogen responsive cell line.

4. An assay according to claim 3 wherein the cell line is a breast cancer cell line.

5. An assay for an inhibitor of estrogen responsive tumour cells which comprises:

a) bringing into contact a cyclin D1, an estrogen receptor and a putative inhibitor compound under conditions where the cyclin and the estrogen receptor, in the absence of inhibitor, are capable of forming a complex; and b) measuring the degree of inhibition of complex formation caused by said inhibitor compound.

6. An assay according to claim 1 or 5 wherein the cyclin D1 is human cyclin D1.

7. An assay according to claim 6 wherein the human cyclin D1 is a mutant cyclin D1 which carries a mutation in the cyclin box and fails to bind to cyclin dependent kinases.

8. An assay according to claim 1 or 5 wherein the estrogen receptor comprises an N-terminal truncation which retains the E/F regions.

9. An assay according to claim 1 or 5 wherein an estrogen is added in step (a).

\* \* \* \* \*